US012741136B2

(12) United States Patent
Zhu et al.

(10) Patent No.: US 12,741,136 B2
(45) Date of Patent: Sep. 22, 2026

(54) BLOOD PUMP

(71) Applicant: SHENZHEN CORE MEDICAL TECHNOLOGY CO., LTD, Shenzhen (CN)

(72) Inventors: Yicheng Zhu, Shenzhen (CN); Shunzhou Yu, Shenzhen (CN)

(73) Assignee: SHENZHEN CORE MEDICAL TECHNOLOGY CO., LTD, Shenzhen (CN)

( * ) Notice: Subject to any disclaimer, the term of this patent is extended or adjusted under 35 U.S.C. 154(b) by 260 days.

(21) Appl. No.: 18/705,933

(22) PCT Filed: Feb. 13, 2023

(86) PCT No.: PCT/CN2023/075748
§ 371 (c)(1),
(2) Date: Apr. 29, 2024

(87) PCT Pub. No.: WO2023/179239
PCT Pub. Date: Sep. 28, 2023

(65) Prior Publication Data

US 2026/0137927 A1 May 21, 2026

(30) Foreign Application Priority Data

Mar. 21, 2022 (CN) ......................... 202210275303.9

(51) Int. Cl.
*A61M 60/00* (2021.01)
*A61M 60/17* (2021.01)
(Continued)

(52) U.S. Cl.
CPC .......... *A61M 60/806* (2021.01); *A61M 60/17* (2021.01); *A61M 60/226* (2021.01); *A61M 60/419* (2021.01); *A61M 60/857* (2021.01)

(58) Field of Classification Search
CPC .................................................. A61M 60/806
See application file for complete search history.

(56) References Cited

U.S. PATENT DOCUMENTS 5,443,503 A 8/1995 Yamane
6,120,537 A 9/2000 Wampler
(Continued)

FOREIGN PATENT DOCUMENTS

CN 2754637 Y 2/2006
CN 103702693 A 4/2014
(Continued)

OTHER PUBLICATIONS

International Search Report issued for International Patent Application No. PCT/CN2023/075748, Date of mailing: Jun. 14, 2023, 9 pages including English translation.
(Continued)

*Primary Examiner* — Joseph M Santos Rodriguez
(74) *Attorney, Agent, or Firm* — HSML P.C.

(57) ABSTRACT

A blood pump (10), comprising: a cannula assembly (100) having an infusion cavity (130); an impeller (200) rotatably provided in the infusion cavity (130), the impeller (200) having an accommodating cavity (234) and a communication hole (232) formed thereon, the communication hole (232) being in communication with the infusion cavity (130) and the accommodating cavity (234); a rotating shaft (300) fixedly connected to the impeller (200), one end of the rotating shaft being provided with a protruding head (320) arranged in the accommodating cavity (234); and a base (400) connected to the cannula assembly (100). The base (400) comprises a support shaft (420), an end face (421) of the support shaft (420) forming a concave cavity (**421*a*) cooperating with the protruding head (320). A flow-through gap (240) is formed between the impeller (200**) and the base
(Continued)

(400), the flow-through gap (240) being in communication with the accommodating cavity (234).

20 Claims, 7 Drawing Sheets

(51) Int. Cl.

| | |
|---|---|
| ***A61M 60/226*** | (2021.01) |
| ***A61M 60/419*** | (2021.01) |
| ***A61M 60/806*** | (2021.01) |
| ***A61M 60/857*** | (2021.01) |

(56) References Cited

U.S. PATENT DOCUMENTS

| | | | |
|---|---|---|---|
| 2014/0275722 | A1 | 9/2014 | Zimmermann et al. |
| 2019/0001034 | A1 | 1/2019 | Taskin et al. |
| 2019/0298902 | A1 | 10/2019 | Siess et al. |
| 2021/0069393 | A1 | 3/2021 | Schauer et al. |
| 2022/0080179 | A1 | 3/2022 | Earles et al. |

FOREIGN PATENT DOCUMENTS

| | | | |
|---|---|---|---|
| CN | 105407937 | A | 3/2016 |
| CN | 107405435 | A | 11/2017 |
| CN | 107921187 | A | 4/2018 |
| CN | 108883216 | A | 11/2018 |
| CN | 110721357 | A | 1/2020 |
| CN | 111870751 | A | 11/2020 |
| CN | 111902168 | A | 11/2020 |
| CN | 112807564 | A | 5/2021 |
| CN | 113663211 | A | 11/2021 |
| CN | 114768085 | A | 7/2022 |
| JP | 2018509223 | A | 4/2018 |
| WO | 0043678 | A1 | 7/2000 |
| WO | 2012115155 | A1 | 8/2012 |
| WO | 2017021465 | A1 | 2/2017 |
| WO | 2020146821 | A1 | 7/2020 |
| WO | 2021113389 | A1 | 6/2021 |

OTHER PUBLICATIONS

Written Opinion issued for International Patent Application No. PCT/CN2023/075748, Date of mailing: Jun. 14, 2023, 5 pages including English machine translation.

Office Action issued for Japanese Patent Application No. 2024-529976, Dispatch date: Mar. 4, 2025, 3 pages.

Office Action issued for Chinese Patent Application No. 202210275303.9, dated Mar. 18, 2025, 10 pages.

Extended European Search Report issued for European Patent Application No. 23773490.0, dated Jul. 11, 2025, 10 pages.

BLOOD PUMP

This application claims priority to Chinese patent application No. 202210275303.9, filed with the China National Intellectual Property Administration on Mar. 21, 2022, the content of which is hereby incorporated by reference in its entirety.

TECHNICAL FIELD

The present disclosure relates to the field of medical device technologies, and in particular, to a blood pump.

BACKGROUND

An intravascular blood pump is a blood pumping device that can be inserted into a patient's heart through a blood vessel of the patient. The intravascular blood pump is placed inside an opening of a heart valve so that blood can flow through the blood pump and into artery blood vessels. However, for traditional intravascular blood pumps, blood clots are easily generated in the blood pump.

SUMMARY

Based on this, the present disclosure provides a blood pump that can reduce a probability of occurrence of blood clots.

Embodiments of a first aspect of the present disclosure provide a blood pump. The blood pump includes:

- a cannula assembly having an infusion cavity;
- an impeller rotatably arranged in the infusion cavity, the impeller having an accommodating cavity and a communication hole formed thereon, the communication hole being in communication with the infusion cavity and the accommodating cavity;
- a rotating shaft fixedly connected to the impeller, an end of the rotating shaft being provided with a raised head located in the accommodating cavity; and
- a base connected to the cannula assembly, the base including a support shaft, an end face of the support shaft forming a concave cavity cooperating with the raised head, a flow-through gap being formed between the impeller and the base, the flow-through gap being in communication with the accommodating cavity.

Details of one or more embodiments of the present disclosure are set forth in the following accompanying drawings and descriptions. Other features, objectives, and advantages of the present disclosure will become apparent from the specification, the accompanying drawings, and the claims.

BRIEF DESCRIPTION OF THE DRAWINGS

In order to more clearly illustrate the technical solutions in embodiments of the present disclosure, the accompanying drawings to be used in the description of the embodiments or the conventional art will be briefly introduced below. It is apparent that, the accompanying drawings in the following description are only some embodiments of the present disclosure, and other accompanying drawings can be obtained by those of ordinary skill in the art from the provided accompanying drawings without creative efforts.

DETAILED DESCRIPTION

In order to make the objectives, technical solutions, and advantages of the present disclosure more clearly understood, the present disclosure is described in further detail below with reference to the accompanying drawings and embodiments. It should be understood that specific embodiments described herein are merely intended to interpret the present disclosure and not intended to limit the present disclosure.

It should be noted that when one element is referred to as "fastened to" or "arranged on" another element, it may be directly disposed on the another element or an intermediate element may exist. When one element is considered to be "connected to" another element, it may be directly connected to the another element or indirectly connected to the another element.

In addition, the terms "first" and "second" are used for descriptive purposes only, which cannot be construed as indicating or implying a relative importance, or implicitly specifying the number of the indicated technical features. Thus, the features defined with "first" and "second" may explicitly or implicitly include one or more features. In the description of the present disclosure, "a plurality of" means two or more, unless specifically stated otherwise.

In order to describe the technical solutions of the present disclosure, description will be made below with reference to specific drawings and embodiments.

Figure 1:
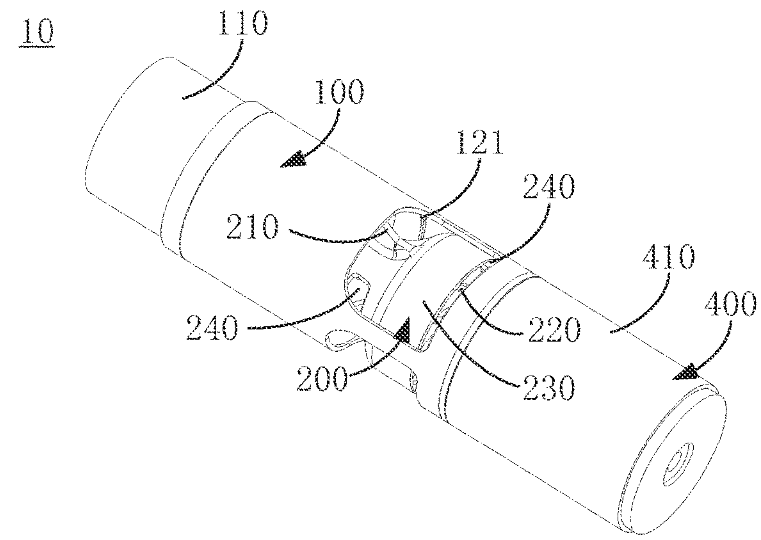
FIG. 1 is a perspective diagram illustrating a blood pump according to an embodiment.
Figure 2:
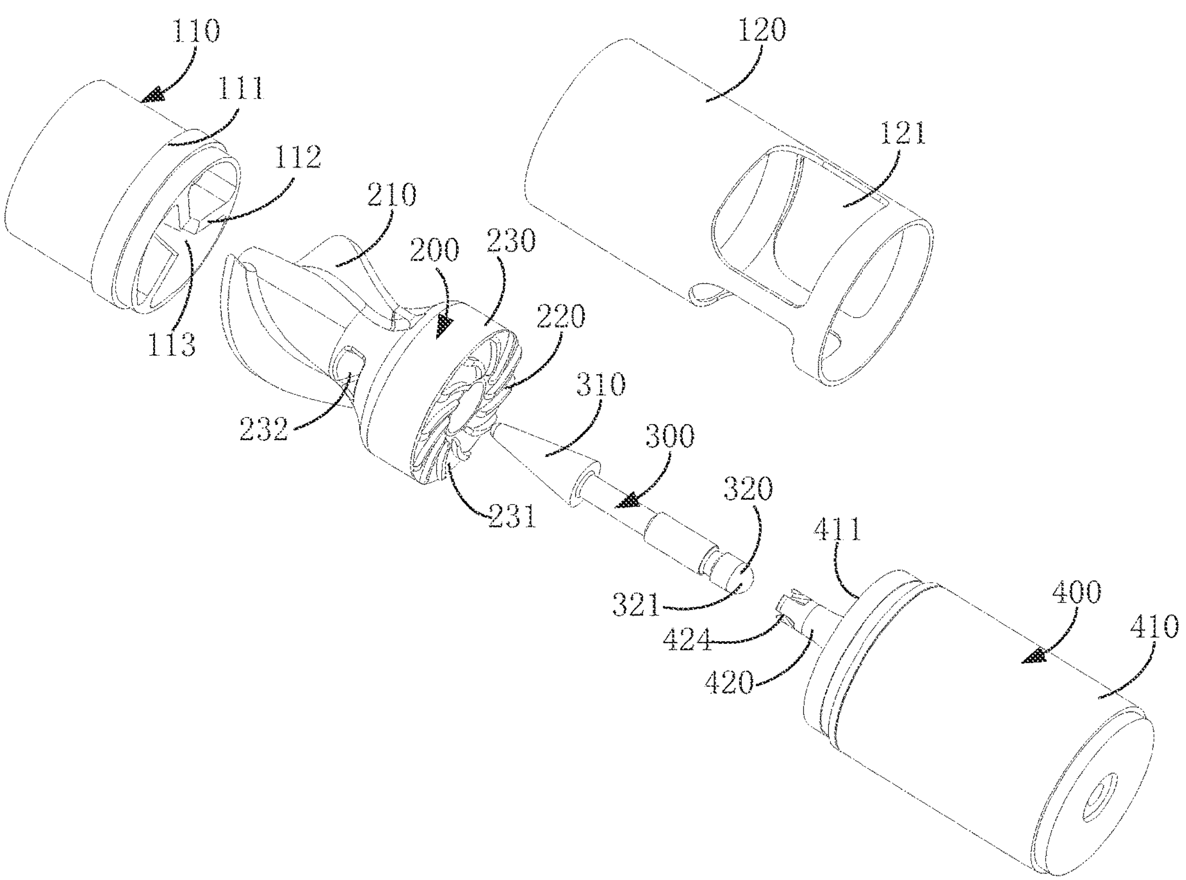
FIG. 2 is an exploded diagram illustrating the whole blood pump shown in FIG. 1.
Figure 3:
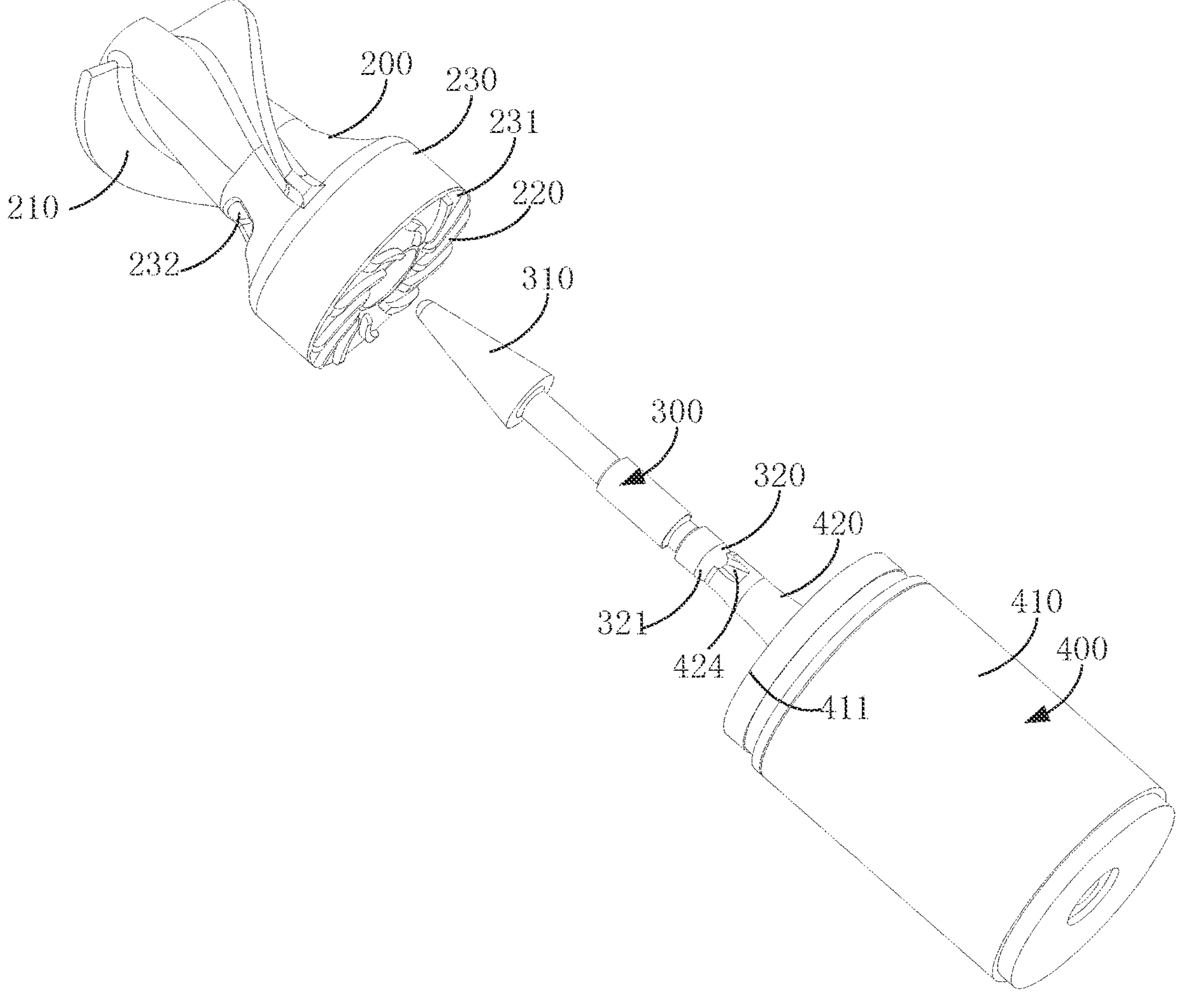
FIG. 3 is an exploded diagram illustrating a part of the blood pump shown in FIG. 1.

Referring to FIG. 1, FIG. 2, and FIG. 3, an embodiment of the present disclosure provides a blood pump 10, and in particular, relates to an intravascular blood pump. The blood pump may be placed at a human heart valve, such as an aortic valve. Under a suction action of the blood pump 10, blood can enter artery blood vessels through the blood pump 10. The blood pump 10 includes a cannula assembly 100, an impeller 200, a rotating shaft 300, and a base 400.

Figure 4:
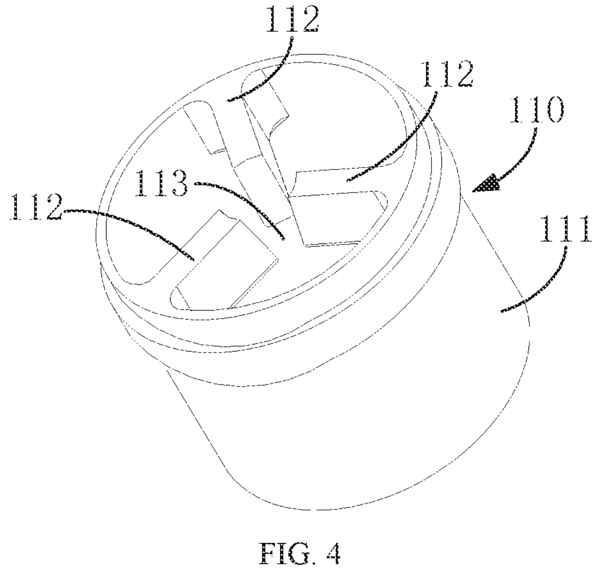
FIG. 4 is a perspective diagram illustrating a first cannula in the blood pump shown in FIG. 1.
Figure 6:
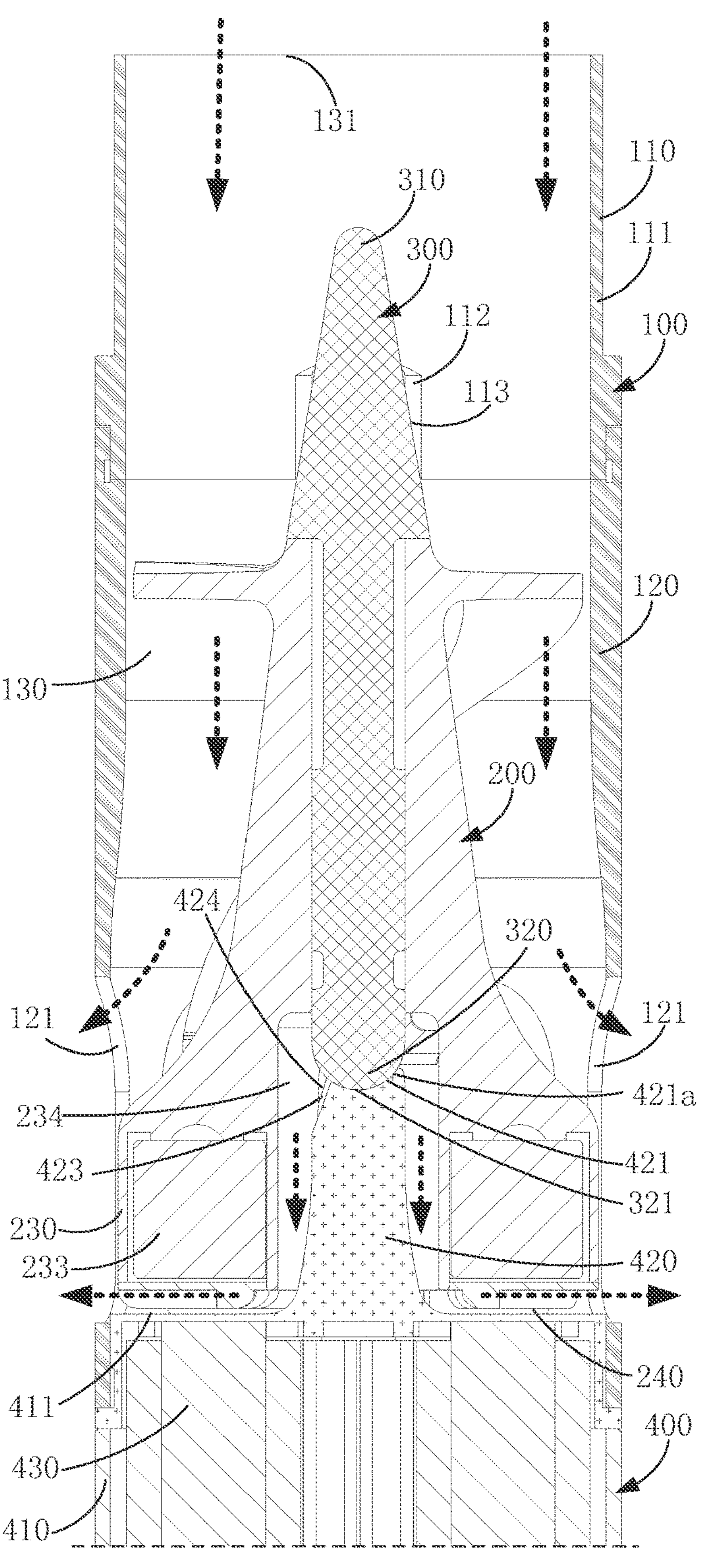
FIG. 6 is a sectional view of the blood pump shown in FIG. 1.

Referring to FIG. 3, FIG. 4, and FIG. 6, in some embodiments, the cannula assembly 100 includes a first cannula 110 and a second cannula 120. The first cannula 110 and the second cannula 120 are coaxially arranged and removably connected to each other. The second cannula 120 is arranged on the base 400. Therefore, the first cannula 110 is further away from the base 400 than the second cannula 120. The first cannula 110 and the second cannula 120 may both be cylindrical, and cavities thereof together form an infusion cavity 130. An input port 131 is formed at an end of the infusion cavity 130 away from the base 400. The input port 131 is located in the first cannula 110. External blood enters the infusion cavity 130 from the input port 131. An output port 121 is arranged in a wall of the second cannula 120. The output port 121 is arranged close to the base 400 and in communication with the infusion cavity 130. Blood in the infusion cavity 130 flows from the output port 121 to the outside of the entire blood pump 10.

The first cannula 110 includes a tube 111 and inner plates 112. The tube 111 is connected to the second cannula 120. The tube 111 and a cavity of the second cannula 120 together form the infusion cavity 130. A plurality of inner plates 112, for example, three or four inner plates 112. The inner plates 112 are arranged on an inner wall surface of the tube 111 (i.e., a cavity wall of the infusion cavity 130) and at a position of the tube 111 close to the second cannula 120. The inner plates 112 are fastened to the inner wall surface of the tube 111, so that the inner plates 112 protrude by a certain length along a radial direction of the tube 111 relative to the inner wall surface. Therefore, the inner plates 112 each have a free end and a fixed end. The fixed end is fastened to the inner wall surface of the tube 111. The fixed end and the inner wall surface are at a distance along the radial direction of the tube 111. The free ends of the inner plates 112 are not in contact with each other, so that the free ends of all the inner plates 112 jointly form a mounting cavity 113. A central axis of the mounting cavity 113 overlaps with a central axis of the tube 111. A diameter of the mounting cavity 113 gradually decreases along a direction in which the second cannula 120 points to the first cannula 110.

The cannula assembly 100 is configured to be in a sectional type including the first cannula 110 and the second cannula 120 removably connected to each other, which can facilitate the mounting of the impeller 200. It may be understood that the cannula assembly 100 is not limited to including the first cannula 110 and the second cannula 120 removably connected to each other. In some embodiments, the first cannula 110 and the second cannula 120 are formed as an inseparable unit. That is, the first cannula 110 and the second cannula 120 are formed integrally. In other words, one cannula replaces both the first cannula 110 and the second cannula 120. Then, the infusion cavity 130 is a cavity of the cannula.

Figure 5:
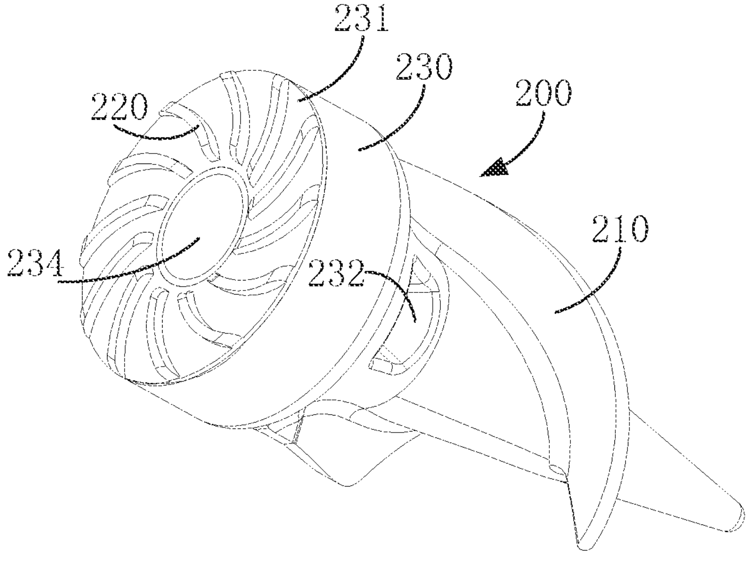
FIG. 5 is a perspective diagram illustrating an impeller in the blood pump shown in FIG. 1.
Figure 7:
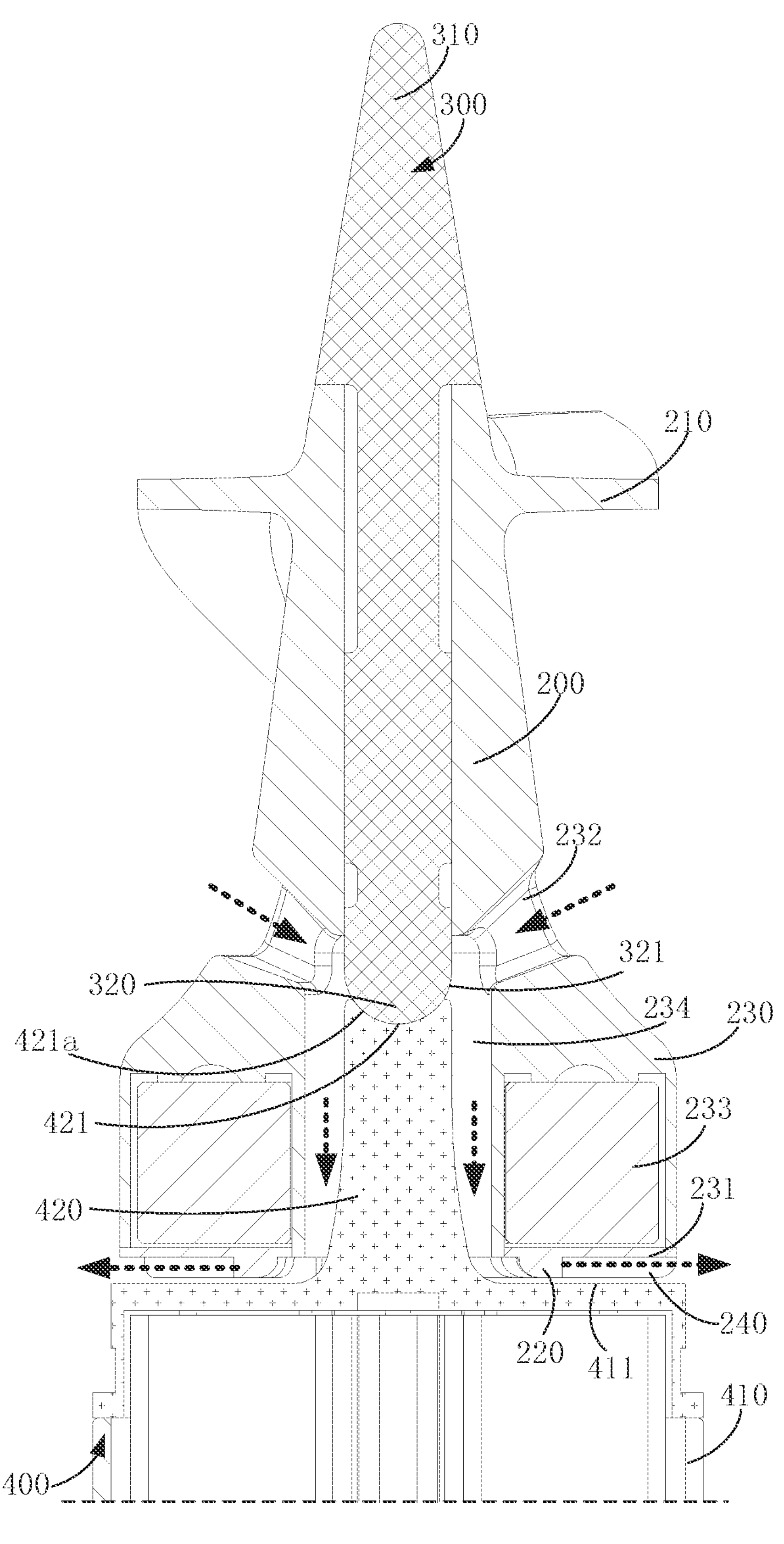
FIG. 7 is a sectional view of the blood pump shown in FIG. 1 with removal of a cannula assembly.

Referring to FIG. 3, FIG. 5, and FIG. 7, in some embodiments, the impeller 200 is rotatably arranged in the infusion cavity 130. A rotation axis of the impeller 200 overlaps with a central axis of the infusion cavity 130, and the rotation axis of the impeller 200 overlaps with a central axis of the impeller 200.

The impeller 200 includes a first blade 210, a second blade 220, and a rotating body 230. Both the first blade 210 and the second blade 220 are fastened to the rotating body 230. The rotating body 230 is provided with a rotor 233. The rotor 233 is a permanent magnet. Specifically, the rotor 233 is accommodated inside the rotating body 230. The rotor 233 may include a Halbach array magnet. The rotor 233 can rotate under an action of a rotating magnetic field generated by the base 400, causing the rotating body 230 to rotate, and then causing both the first blade 210 and the second blade 220 to rotate with the rotating body 230. The rotating body 230 is provided with a communication hole 232 and an accommodating cavity 234. The communication hole 232 is in communication with the accommodating cavity 234 and the infusion cavity 130. The blood in the infusion cavity 130 may flow into the accommodating cavity 234 through the communication hole 232. Specifically, the accommodating cavity 234 extends along the central axis of the impeller 200, and the communication hole 232 extends in a direction inclined relative to the central axis of the impeller 200.

Referring to FIG. 6 and FIG. 7, for convenience of description, a central axis of the communication hole 232 is referred to as a first central axis, and the central axis of the impeller 200 is referred to as a second central axis. The first central axis and the second axis are arranged at an acute angle. A flow direction of the blood in the communication hole 232 is taken as a reference direction. Then, along a direction in which blood flows in the communication hole 232, an aperture size of the communication hole 232 gradually decreases, and a distance from the first central axis to the second central axis gradually decreases. Generally, the communication hole 232 is generally tapered, so that the communication hole 232 has an opening with a small aperture size and an opening with a large aperture size. The opening with the small aperture size is in communication with the accommodating cavity 234, and the opening with the large aperture size is in communication with the infusion cavity 130. In this way, the communication hole 232 has a good guiding effect on the blood, allowing the blood in the infusion cavity 130 to enter the accommodating cavity 234 at an appropriate flow rate.

Referring to FIG. 5, FIG. 6, and FIG. 7, the first blade 210 may be in the shape of a spiral and generally extend along an axial direction of the rotating body 230, and the first blade 210 is located in the infusion cavity 130. When the first blade 210 rotates with the rotating body 230, the first blade 210 may generate a pumping force, causing external blood to enter the infusion cavity 130 from the input port 131 and be discharged from the output port 121.

The rotating body 230 further has a mounting surface 231, and the mounting surface 231 is arranged towards the base 400. The mounting surface 231 and the base 400 are arranged at intervals along the axial direction of the rotating body 230. A gap is formed between the mounting surface 231 and the base 400. The gap is referred to as a flow-through gap 240. The flow-through gap 240 is in communication with the accommodating cavity 234. Specifically, a position of the flow-through gap 240 corresponds to that of the output port 121. The second blade 220 is arranged on the mounting surface 231 and extends along a radial direction of the rotating body 230. The second blade 220 is at least partially accommodated in the flow-through gap 240. In the illustrated embodiments, the second blade 220 is wholly located in the flow-through gap 240. A plurality of second blades 220 are provided. The second blades 220 may be arranged at intervals along a circumferential direction of the rotating body 230. The mounting surface 231 is perpendicular to the central axis of the impeller 200. When the second blade 220 rotates with the rotating body 230, the second blade 220 may also generate a pumping force, so that the blood in the accommodating cavity 234 is quickly discharged from the output port 121 through the flow-through gap 240 under an action of the pumping force.

Referring to FIG. 6 and FIG. 7, when the entire impeller 200 rotates, external blood may enter the infusion cavity 130 from the input port 131, and the blood in the infusion cavity 130 may be divided into two streams. A first stream of blood is directly discharged from the output port 121. A flow trajectory of the first stream of blood may be referred to as: the infusion cavity 130—the output port 121. A second stream of blood enters the accommodating cavity 234 through the communication hole 232, flows through the flow-through gap 240, and then is discharged from the output port 121. Therefore, a flow trajectory of the second stream of blood may be referred to as: the infusion cavity 130—the communication hole 232—the accommodating cavity 234—the flow-through gap 240—the output port 121. Dotted arrows in FIG. 6 and FIG. 7 point to the flow trajectories of the blood. Since the impeller 200 includes the second blade 220, under the action of the pumping force generated by the second blade 220, a speed and a flow rate of the blood flowing through the accommodating cavity 234 can be increased.

Referring to FIG. 3, FIG. 6, and FIG. 7, in some embodiments, the rotating shaft 300 is fixedly connected to the impeller 200. The rotating shaft 300 is arranged so as to pass through the rotating body 230, a central axis of the rotating shaft 300 overlaps with the central axis of the impeller 200, and the rotating shaft 300 may be fastened to the rotating body 230 by bonding. An end of the rotating shaft 300 away from the base 400 is a cone 310, the cone 310 extends into the first cannula 110, and the cone 310 fits the mounting cavity 113 in the first cannula 110. When the rotating shaft 300 rotates with the impeller 200, the cone 310 may rotate in the mounting cavity 113.

The mounting cavity 113 matches the cone 310 in shape and size, which, on the one hand, can axially limit the rotating shaft 300 when the rotating shaft 300 fits the mounting cavity 113, and on the other hand, can provide a fulcrum for an end of the rotating shaft 300 to improve stability of the rotating shaft 300 and the impeller 200 during rotation. The free end of the inner plate 112 may be coated with a diamond coating, and the rotating shaft 300 may be made of a ceramic material. When the rotating shaft 300 is in contact with the diamond coating, the frictional resistance of the rotating shaft 300 during rotation may be reduced, and smoothness of the rotating shaft 300 and the impeller 200 during rotation may be improved.

The rotating shaft 300 also includes a raised head 320. The raised head 320 is located at an end of the rotating shaft 300 close to the base 400. The raised head 320 may be in the shape of a sphere or a spherical segment. The raised head 320 may alternatively be in the shape of a cylinder or the like. The raised head 320 is accommodated in the accommodating cavity 234. The raised head 320 has a convex surface 321. The convex surface 321 protrudes along an axial direction of the rotating shaft 300, and the convex surface 321 abuts against the base 400.

Referring to FIG. 3, FIG. 6, and FIG. 7, in some embodiments, the base 400 includes a carrying body 410, the support shaft 420, and a stator 430. The stator 430 is arranged in the carrying body 410. When electric energy is supplied to the stator 430, the stator 430 can generate a rotating magnetic field, thereby driving the rotor 233 to rotate to drive the entire impeller 200 to rotate. The second cannula 120 sleeves and is fastened to the carrying body 410. The carrying body 410 has a support surface 411. The support surface 411 and the mounting surface 231 on the rotating body 230 are arranged at intervals. Therefore, the flow-through gap 240 is located between the support surface 411 and the mounting surface 231. The support shaft 420 is connected to the support surface 411 and protrudes relative to the support surface 411, so that the support shaft 420 protrudes relative to the support surface 411 by a certain length along an axial direction of the carrying body 410. The support shaft 420 is accommodated in the accommodating cavity 234. The support shaft 420 and a cavity wall of the accommodating cavity 234 are arranged at intervals. That is, the support shaft 420 does not form a contact relationship with the cavity wall of the accommodating cavity 234. In other words, the support shaft 420 does not fill the entire accommodating cavity 234, so as to ensure that there is still space for the blood to flow in the accommodating cavity 234. Central axes of the support shaft 420 and the rotating shaft 300 overlap, and an end of the support shaft 420 abuts against the rotating shaft 300. That is, the support shaft 420 supports the rotating shaft 300 and the impeller 200, and ensures that the above flow-through gap 240 exists between the mounting surface 231 and the support surface 411.

Figure 8:
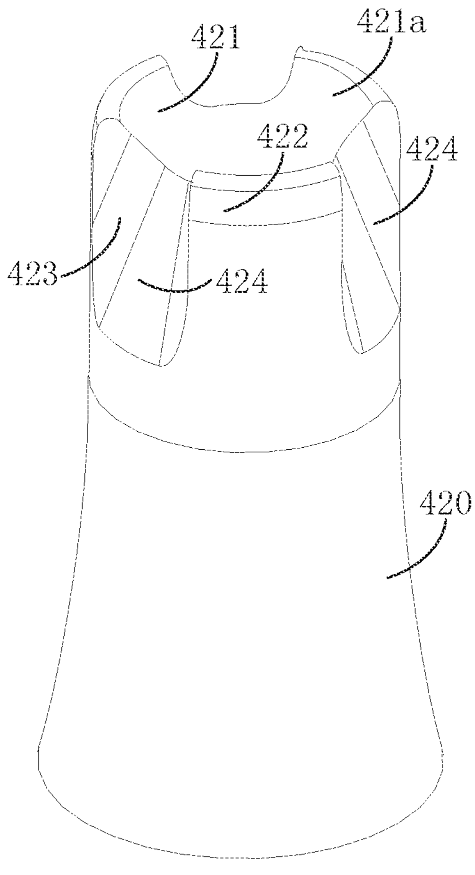
FIG. 8 is a perspective diagram illustrating a support shaft in the blood pump shown in FIG. 1.
Figure 9:
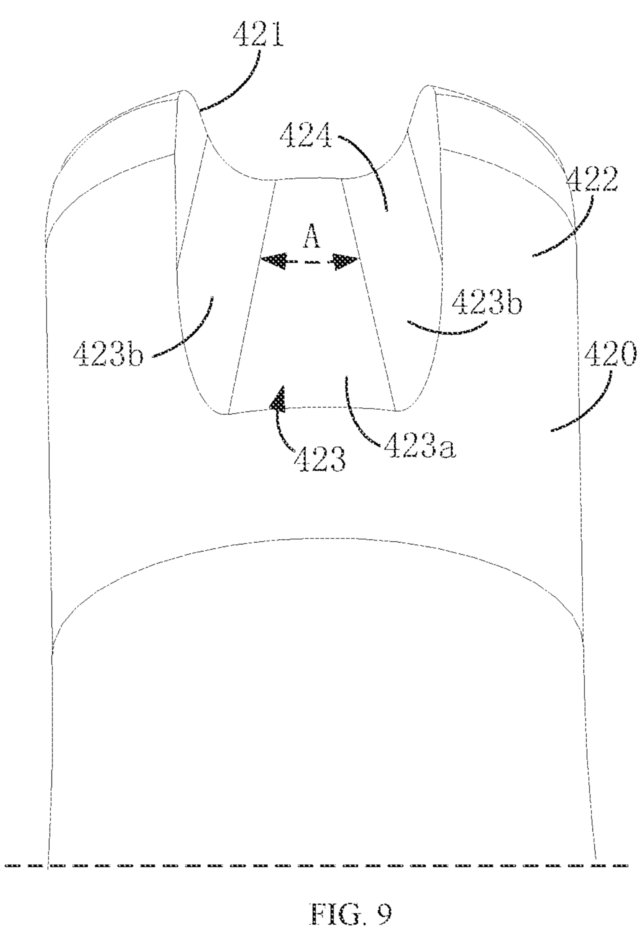
FIG. 9 is a perspective diagram illustrating the support shaft shown in FIG. 8 from another perspective.

Referring to FIG. 7, FIG. 8, and FIG. 9, an end of the support shaft 420 away from the support surface 411 has an end face 421. The end face 421 forms a concave cavity 421*a* surrounded by the end face 421. The end face 421 is recessed by a certain depth along the axial direction of the support shaft 420 and is in a recessed state. A shape of the concave cavity 421*a* matches that of the raised head 320. The raised head 320 can cooperate with the concave cavity 421*a*. The raised head 320 can rotate in the concave cavity 421*a*, and the concave cavity 421*a* can play a good radial positioning role in the rotation of the raised head 320 and the entire rotating shaft 300. Since the raised head 320 and the concave cavity 421*a* cooperate with each other, the convex surface 321 of the raised head 320 and the end face 421 abut against each other. The convex surface 321 is at least partially accommodated in the concave cavity 421*a*. For example, the convex surface 321 may be entirely located within the concave cavity 421*a*. In another example, one part of the convex surface 321 is located inside the concave cavity 421*a*, and the other part of the convex surface 321 is located outside the concave cavity 421*a*. The opening with the small aperture size of the communication hole 232 is further away from the flow-through gap 240 than the end face 421 of the support shaft 420. Generally, the opening with the small aperture size of the communication hole 232 is located obliquely above the end face 421. When the blood in the infusion cavity 130 flows into the accommodating cavity 234 through the communication hole 232, the blood flowing out from the opening with the small aperture size of the communication hole 232 may flow to the above raised head 320 and the end face 421 well.

In some embodiments, the rotating shaft 300 is made of a ceramic material, and a diamond layer is arranged on the end face 421 of the support shaft 420, which may reduce frictional resistance of the rotating shaft 300 during the rotation and improve smoothness of the rotating shaft 300 and the impeller 200 during the rotation.

When the blood enters the accommodating cavity 234, since the rotating shaft 300 cooperates with the concave cavity 421*a* on the support shaft 420 through the raised head 320, relative positions and specific shapes of the convex surface 321 and the end face 421 may well guide the blood, which may increase a chance of the blood contacting an abutment position between the support shaft 420 and the rotating shaft 300, making it easier for the blood to flow between the support shaft 420 and the rotating shaft 300. Therefore, on the one hand, the blood may have more chances to effectively flush the abutment position between the support shaft 420 and the rotating shaft 300 to prevent formation of blood clots due to long-time accumulation of viscous or coagulated matter in the blood at the abutment position. On the other hand, an increased speed and flow rate of the blood flowing through the abutment position can improve fluidity of the blood and also improve a flushing force of the blood at the abutment position, further preventing the formation of the blood clots due to the accumulation of the viscous or coagulated matter at the abutment position. Therefore, the cooperation between the raised head 320 and the concave cavity 421*a* can effectively reduce a probability of occurrence of the blood clots.

It should be pointed out that, in view of the existence of the second blade 220, a speed and a flow rate of the blood flowing through the accommodating cavity 234 may be increased, thereby further increasing the fluidity and the flushing force of the blood in the accommodating cavity 234 and also effectively reducing a probability of occurrence of the blood clots in the accommodating cavity 234. The diamond layer attached to the end face 421 may also reduce flow resistance of the blood in the concave cavity 421*a*, enhance the fluidity and the flushing force of the blood, and reduce a probability of formation of the blood clots, which also reduces heat generated by friction between the rotating shaft 300 and the support shaft 420, and prolongs the service life of the entire blood pump 10. Certainly, the blood flowing between the rotating shaft 300 and the support shaft 420 may also take away frictional heat, further prolonging the service life of the blood pump 10. When the flow rate of the blood in the accommodating cavity 234 is larger, more frictional heat can be taken away.

In some embodiments, the support shaft 420 also has an outer peripheral surface 422 and a guide surface 423. The outer peripheral surface 422 is an annular surface. The outer peripheral surface 422 is connected to a periphery of the end face 421 so that the outer peripheral surface 422 is arranged around the end face 421. An end of the support shaft 420 away from the support surface 411 is recessed to form a guide groove 424. The guide groove 424 extends through the end face 421 and the outer peripheral surface 422, and is in communication with the concave cavity 421*a*. It is clear that the guide groove 424 is also in communication with the accommodating cavity 234. A plurality of guide grooves 424 are provided, which may be, for example, two, three, four, or more. The plurality of guide grooves 424 are evenly arranged at intervals along a circumferential direction of the support shaft 420. The guide surface 423 is connected between the outer peripheral surface 422 and the end face 421 and defines a partial boundary of the guide groove 424. The guide surface 423 is arranged obliquely relative to a central axis of the support shaft 420. The guide surface 423 intersects with the central axis of the support shaft 420 at an acute angle. Along a direction from an end away from the support surface 411 to an end close to the support surface 411, a distance between the guide surface 423 and the central axis of the support shaft 420 gradually increases. In other words, the guide surface 423 gradually moves away from the central axis of the support shaft 420 in a direction away from the rotating shaft 300. Generally, the guide surface 423 is arranged obliquely downwards, so that a depression depth of a part of the guide groove 424 close to the end face 421 is relatively large, while a depression depth of a part of the guide groove 424 away from the end face 421 is relatively small.

Figure 10:
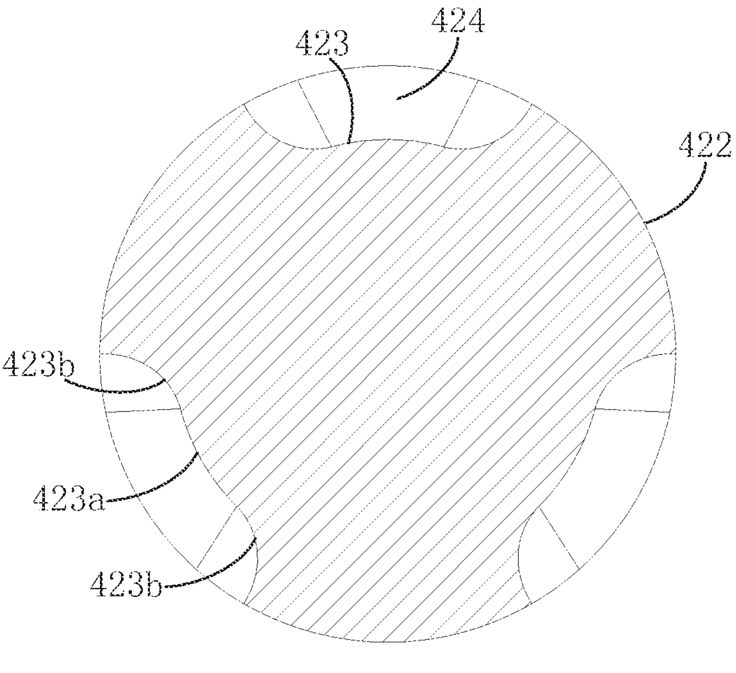
FIG. 10 is a schematic diagram illustrating a cross section of the support shaft shown in FIG. 8.

Referring to FIG. 8, FIG. 9, and FIG. 10, the guide surface 423 includes a middle guide section 423*a* and two edge guide sections 423*b*, the middle guide section 423*a* and the two edge guide sections 423*b* are arranged along the circumferential direction of the support shaft 420, and the middle guide section 423*a* is connected between the two edge guide sections 423*b*. Specifically, the middle guide section 423*a* protrudes in a direction away from the central axis of the support shaft 420, so that the middle guide section 423*a* is a raised surface. The edge guide sections 423*b* are recessed in a direction close to the central axis of the support shaft 420, so that the edge guide sections 423*b* are concave surfaces, which may be understood as that the guide groove 424 is high in the middle and low on the edge. Along the direction away from the rotating shaft 300, a length A occupied by the middle guide section 423*a* in the circumferential direction of the support shaft 420 gradually increases, which may be generally understood that the middle guide section 423*a* is roughly a convex arc-shaped isosceles trapezoid.

In view of the arrangement of the guide groove 424, the guide groove 424 extends through the end face 421 of the support shaft 420, which can reduce a contact area between the convex surface 321 of the raised head 320 and the support shaft 420. Moreover, the guide surface 423 is arranged in an inclined state, so that the depression depth of the part of the guide groove 424 close to the end face 421 is relatively large, and then an area of the end face 421 removed due to penetration by the guide groove 424 is relatively large, which further reduces the contact area between the convex surface 321 and the support shaft 420 and finally reduces a probability of formation of the blood clots. Moreover, the blood in the accommodating cavity 234 flows in the guide groove 424, so that the blood in the guide groove 424 may increase a chance of contact with the abutment position between the support shaft 420 and the rotating shaft 300, which further reduces the probability of formation of the blood clots.

Since the middle guide section 423*a* is a raised surface and the edge guide sections 423*b* are concave surfaces, when the blood flows in the guide groove 424, the blood may flow from a high position in the middle to a low position on the edge. That is, the blood may flow from the middle guide section 423*a* to the edge guide sections 423*b*. In short, during the flow from top to bottom along the axial direction of the support shaft 420, the blood may also flow left and right along the circumferential direction of the support shaft 420, which may increase turbulence of the blood during the flow, causing the blood to generate vortices, thereby appropriately prolonging a flushing time of the blood at the abutment position between the support shaft 420 and the rotating shaft 300 and increasing the flushing force, preventing "stuck blood" in a seam space, and reducing the probability of formation of the blood clots. When the middle guide section 423*a* is roughly in the shape of a convex arc-shaped isosceles trapezoid, the blood in the edge guide section 423*b* flows obliquely downwards in a direction that is at an angle to the axial direction of the support shaft 420, and the blood flow of the edge guide section 423*b* has both a branching direction along the axial direction of the support shaft 420 and a branching direction along the circumferential direction of the support shaft 420, which may also enhance vortex strength of the blood and reduce the probability of formation of the blood clots.

The foregoing embodiments are merely intended to describe the technical solutions of the present disclosure, but not to limit the present disclosure. Although the present disclosure is described in detail with reference to the foregoing embodiments, those of ordinary skill in the art should understand that they may still make modifications to the technical solutions described in the foregoing embodiments or make equivalent replacements to some technical features thereof, without departing from the spirit and scope of the technical solutions of the embodiments of the present disclosure, all of which fall within the protection scope of the present disclosure.

The invention claimed is:

1. A blood pump, comprising:

a cannula assembly having an infusion cavity;

an impeller rotatably arranged in the infusion cavity, the impeller having an accommodating cavity and a communication hole formed thereon, the communication hole being in communication with the infusion cavity and the accommodating cavity;

a rotating shaft fixedly connected to the impeller, an end of the rotating shaft being provided with a raised head located in the accommodating cavity; and a base connected to the cannula assembly, the base comprising a support shaft, an end face of the support shaft forming a concave cavity cooperating with the raised head, a flow-through gap being formed between the impeller and the base, the flow-through gap being in communication with the accommodating cavity.

2. The blood pump according to claim 1, wherein the raised head is in a shape of a sphere or a spherical segment.

3. The blood pump according to claim 1, wherein the raised head has a convex surface abutting against the end face, and at least part of the convex surface is accommodated in the concave cavity.

4. The blood pump according to claim 1, wherein the support shaft further has an outer peripheral surface and a guide surface, the outer peripheral surface being located in the accommodating cavity and arranged around the end face, and the support shaft is further provided with a guide groove extending through the outer peripheral surface and the end face and in communication with the concave cavity, the guide surface being connected to the outer peripheral surface and the end face and defining a partial boundary of the guide groove.

5. The blood pump according to claim 4, wherein a distance between the guide surface and a central axis of the support shaft gradually increases along a direction away from the rotating shaft.

6. The blood pump according to claim 4, wherein the guide surface comprises a middle guide section and two edge guide sections arranged along a circumferential direction of the support shaft, the middle guide section being connected between the two edge guide sections, the middle guide section protruding in a direction away from a central axis of the support shaft, and the edge guide sections being recessed in a direction close to the central axis of the support shaft.

7. The blood pump according to claim 6, wherein a length occupied by the middle guide section in the circumferential direction of the support shaft gradually increases along a direction away from the rotating shaft.

8. The blood pump according to claim 4, wherein a plurality of guide grooves are provided, the plurality of guide grooves being arranged at intervals along a circumferential direction of the support shaft.

9. The blood pump according to claim 1, wherein the base has a support surface, the support shaft being connected to the support surface and protruding relative to the support surface, the impeller further comprises a rotating body, and a first blade and a second blade that are arranged on the rotating body, the accommodating cavity is arranged in the rotating body, and the flow-through gap is located between the rotating body and the support surface, the first blade being located in the infusion cavity, and the second blade being at least partially located in the flow-through gap.

10. The blood pump according to claim 9, wherein the rotating body further has a mounting surface, the mounting surface being arranged towards the support surface, the mounting surface and the support surface being arranged at intervals along an axial direction of the rotating body, and at least part of the flow-through gap is located between the mounting surface and the support surface.

11. The blood pump according to claim 10, wherein the mounting surface is perpendicular to a central axis of the impeller, the second blade is arranged on the mounting surface and extends along a radial direction of the rotating body, and a plurality of second blades are provided, the plurality of second blades being arranged at intervals along a circumferential direction of the rotating body.

12. The blood pump according to claim 9, wherein the base comprises a carrying body, the support shaft, and a stator, the stator being arranged in the carrying body, the stator, when powered on, being capable of generating a rotating magnetic field to drive the impeller to rotate, and the cannula assembly sleeves and is fastened to the carrying body, the carrying body having the support surface.

13. The blood pump according to claim 1, wherein the communication hole has two openings, the two openings being in communication with the accommodating cavity and the infusion cavity respectively, the opening in communication with the accommodating cavity facing the concave cavity, and the opening in communication with the accommodating cavity being further away from the flow-through gap than the end face of the support shaft.

14. The blood pump according to claim 1, wherein the communication hole has an opening with a small aperture size and an opening with a large aperture size, the opening with the small aperture size being in communication with the accommodating cavity, and the opening with the large aperture size being in communication with the infusion cavity.

15. The blood pump according to claim 1, wherein a plurality of inner plates are arranged in the infusion cavity, the inner plurality of plates protruding relative to a cavity wall surface of the infusion cavity, the plurality of inner plates forming a mounting cavity in rotation fit with the rotating shaft.

16. The blood pump according to claim 15, wherein an end of the rotating shaft away from the base is a cone, the cone fitting the mounting cavity.

17. The blood pump according to claim 16, wherein the cannula assembly comprises a first cannula and a second cannula, the first cannula comprising a tube and the inner plates, the tube and the second cannula being coaxially arranged and removably connected to each other; and wherein the second cannula is arranged on the base, and an aperture size of the mounting cavity gradually decreases along a direction in which the second cannula points to the first cannula.

18. The blood pump according to claim 1, wherein the cannula assembly further comprises an output port in communication with the infusion cavity, the output port being located at an end of the cannula assembly close to the base, and a position of the flow-through gap corresponds to that of the output port.

19. The blood pump according to claim 1, wherein a central axis of the communication hole is a first central axis, and a central axis of the impeller is a second central axis arranged at an acute angle with the first central axis; and wherein along a direction in which a fluid flows in the communication hole, an aperture size of the communication hole gradually decreases, and a distance from the first central axis to the second central axis gradually decreases.

20. The blood pump according to claim 1, wherein the accommodating cavity extends along a central axis of the impeller, and the communication hole extends in a direction inclined relative to the central axis of the impeller.

* * * * *